United States Patent [19]

Woo

[11] 4,239,694
[45] Dec. 16, 1980

[54] BIS-DICYANOALKYL ARENE COMPOUNDS

[75] Inventor: Edmund P. Woo, Midland, Mich.

[73] Assignee: The Dow Chemical Company, Midland, Mich.

[21] Appl. No.: 107,473

[22] Filed: Dec. 26, 1979

[51] Int. Cl.$^3$ .................. C07C 121/66; C07C 121/75
[52] U.S. Cl. ........................... 260/465 D; 260/465 F; 260/465 G; 260/465 H
[58] Field of Search ........... 260/465 D, 465 H, 465 F, 260/465 G

[56] References Cited

U.S. PATENT DOCUMENTS

| | | | |
|---|---|---|---|
| 3,153,658 | 10/1964 | Hertler | 260/465 D X |
| 3,293,278 | 12/1966 | Zienty et al. | 260/465 H |
| 3,355,464 | 11/1967 | Zienty et al. | 260/347.3 |
| 3,504,001 | 3/1970 | Marten | 260/465 H X |
| 4,130,579 | 12/1978 | Frazer et al. | 260/465 H |

OTHER PUBLICATIONS

Perekalin et al., J. Gen. Chem. USSR, Eng. Ed., vol. 28, pp. 1861–1867 (1958).
Hedge et al., J. Org. Chem., vol. 26, pp. 3166–3170 (1961).

*Primary Examiner*—Dolph H. Torrence
*Attorney, Agent, or Firm*—Douglas N. Deline

[57] ABSTRACT

Novel bis-dicyanoalkyl arene compounds are described of the formula

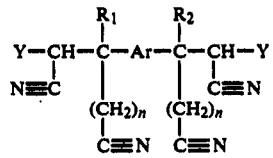

wherein Ar, $R_1$ and $R_2$ are named substituents, Y is hydrogen or

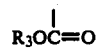

where $R_3$ is an alkyl radical having 1 to 10 carbon atoms, and both n's are zeros or ones; provided that when both n's are zeros, Y is

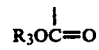

and when both n's are ones, Y is hydrogen.

10 Claims, No Drawings

BIS-DICYANOALKYL ARENE COMPOUNDS

BACKGROUND OF THE INVENTION

The invention relates to new chemical compounds and particularly to derivatives of aromatic dicarbonyl compounds. These derivatives, more specifically are tetracyano derivatives of aromatic dicarbonyl compounds and exhibit utility as synthetic resin intermediates.

DESCRIPTION OF THE PRIOR ART

U.S. Pat. Nos. 3,293,278 and 3,355,464 teach certain derivatives of diphenylethylbenzene, specifically derivatives of the formula

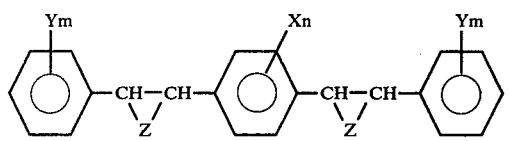

wherein Z is a divalent moiety including

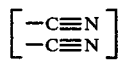

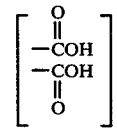

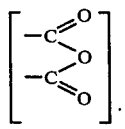

V. V. Perekalin et al. in J. Gen. Chem. USSR, Eng. Ed., 28, 1861 (1958) disclosed the synthesis of certain bis(nitroalkyl)benzene compounds and their derivatives. Included were compounds of the formula

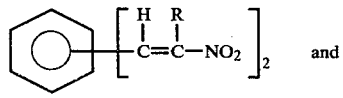 and

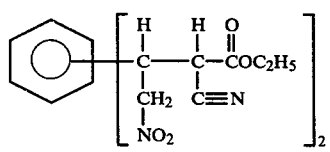

Hedge and coworkers in J. Org. Chem. 26, 3167 (1961) reported that the condensation of a dicarbonyl compound with a very active methylene compound did not produce the 1:4 condensate, but rather only the 1:3 condensate. Thus, when isophthaldehyde and terephthaldehyde were contacted with excess isopropylidinyl malonate in dimethylformamide the product in either case resulted from both an aldol reaction and a Michael reaction at one aldehyde functionality but only an aldol reaction at the remaining aldehyde functionality.

SUMMARY OF THE INVENTION

The invention comprises certain bis-dicyanoalkyl arene compounds of the formula

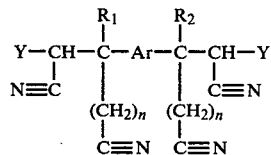

wherein Ar is a $C_{6-20}$ arylene radical selected from the group consisting of

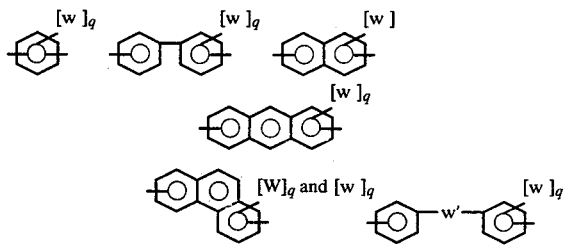

wherein W in each occurrence is halo, nitro, or a $C_{1-10}$ radical selected from alkyl, aryl, alkaryl, aralkyl, haloalkyl, haloaryl, aryloxy and alkoxy; q is an integer from zero to 4; and w' is oxygen, sulfur, alkylene, oxyalkylene, alkylenedioxy, or polyoxyalkylene; $R_1$, $R_2$ individually are hydrogen, or alkyl, aryl, aralkyl, or alkaryl radicals containing up to 10 carbon atoms, Y is hydrogen or

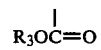

wherein $R_3$ is an alkyl radical containing 1 to 10 carbon atoms, and both n's are zeros or ones; provided that when both n's are zeros, Y is

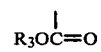

and when both n's are ones, Y is hydrogen. Also included in the invention is a novel process for producing compounds of formula I wherein both n's are 1. The compounds are useful as precursors in the manufacture of polymeric substances. For example, they may be easily hydrolyzed to a corresponding tetracarboxylic acid by refluxing with concentrated hydrochloric a sulfuric acid. The resulting tetracarboxylic acid may be next converted to the corresonding dianhydride by heating under reduced pressure and thereafter reacted with a diamine to form a polyimide. This reaction is well-known in the art.

DETAILED DESCRIPTION OF THE INVENTION

The compounds of formula (I) wherein n is zero are prepared by an initial Knovenagel condensation of an alkyl cyanoacetate and an aromatic dicarbonyl compound, either an aromatic dialdehyde or an aromatic diketone. The aromatic diketone may be symmetrical or unsymmetrical. Suitable alkyl cyanoacetate reactants are methyl cyanoacetate, ethyl cyanoacetate, propyl cyanoacetate, butyl cyanoacetate, pentyl cyanoacetate, hexyl cyanoacetate, heptyl cyanoacetate, octyl cyanoacetate, nonyl cyanoacetate, and decyl cyanoacetate. A preferred alkyl cyanoacetate reactant is ethyl cyanoacetate.

Suitable aromatic dicarbonyl compounds are all compounds of the formula

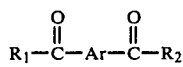

wherein $R_1$, $R_2$ and Ar are as previously defined.

Preferred aromatic dicarbonyl compounds are dialdehyde and diketone derivatives of benzene. Most preferred aromatic dicarbonyl compounds are terephthaldehyde, isophthaldehyde, and p-diacetylbenzene.

The condensation takes place as is known in an inert organic solvent in the presence of a basic catalyst, for example, ethylenediamine, pyridine, piperidine or a buffered catalyst system composed of an amine and the corresponding conjugate acid. Suitable solvents include anhydrous alcohols, e.g., methanol, ethanol, etc. The reaction proceeds smoothly at atmospheric pressure, however, reduced or elevated pressures may also be employed if desired. The condensation may be allowed to proceed at ambient temperatures for a sufficient amount of time to produce a precipitate, illustratively about one hour or more. Reaction vessels of ordinary design and construction, e.g., glass flasks may conveniently be used. The product is recovered by filtration or decanting of liquid and may be recrystallized as for example from toluene, benzene or acetone.

The next step of the synthesis is to form the bis-dicyanoester. This may be done in two steps by reacting the bis(2-carbalkoxy-2-cyanoethenyl)arene produced in the initial Knovenagel condensation with an alkali metal cyanide followed by acidification. Alternatively one may contact HCN directly with the bis(2-carbalkoxy-2cyanoethenyl)arene, as for example by contacting gaseous HCN with the dicyano compound in an inert liquid medium. Again ordinary reaction equipment and parameters may be employed, exercising caution of course when handling the dangerous cyanide reactants.

The bis[(alkoxy carbonyl)dicyanoethyl]arene compounds are easily recovered as they precipitate from the acidic solution. They may be washed and purified, for example by recrystallization from alcoholic solvents, and used as polymeric precursors or to produce tetraamines, for example, by a selective saponification followed by reduction, according to well-known techniques in the art.

The compounds of formula (I) wherein n is 1 are prepared by an initial Knovenagel condensation of four equivalents of cyanoacetic acid with an aromatic dicarbonyl compound, either an aromatic dialdehyde or an aromatic diketone. The aromatic diketone may be symmetrical or unsymmetrical.

Suitable aromatic dicarbonyl compounds are those compounds previously mentioned. A preferred dicarbonyl compound is terephthaldehyde.

The reactants are combined in at least a 4:1 mole ratio of cyanoacetic acid and aromatic dicarbonyl compound. Preferably, an excess of cyanoacetic acid is present.

The condensation takes place in pyridine solvent, preferably in the presence of a catalyst, for example, piperidine. The condensation takes place at an elevated temperature. Preferable are temperatures from about 80° to 200° C., most preferably, from 100° to 150° C. The reaction proceeds smoothly at atmospheric pressure, however, reduced or elevated pressures may also be employed if desired. Reaction times of from several hours to 20 hours or more may be employed. Reaction vessels of ordinary design and construction, e.g., glass flasks may conveniently be used. The resulting product may be recovered by ordinary techniques, for example, by solvent evaporation under reduced pressure, and may be recrystallized if desired.

SPECIFIC EMBODIMENTS OF THE INVENTION

Having described my invention the following examples are provided as further illustrative of my present invention and are not to be construed as limiting.

EXAMPLE 1—1,4-bis(2-carbethoxy-1,2-dicyanoethyl)benzene

A quantity of 1,4-bis(2-carbethoxy-2-cyanoethenyl)benzene was prepared according to the method of Perekalin and Lerner. Accordingly, a drop of piperidine was added to quantities of ethyl cyanoacetate and terephthaldehyde in an excess of anhydrous ethanol accompanied by stirring at ambient temperature. A clear solution slowly formed yielding a crystalline condensation product upon further reaction. After 10 hours the condensation was terminated, the precipitate collected by filtration, and washed with methanol. The product, in the form of yellowish-green needles was soluble in hot benzene and acetone but insoluble in ethanol.

Next, 32.4 g (0.1 mole) of this diester was stirred with sodium cyanide (19.6 g, 0.4 mole) in 400 ml of 50 percent aqueous ethanol at ambient temperature, in a 1-liter glass flask. After 1.5 hours the solution was acidified by adding excess concentrated HCl. The product, 1,4-bis(2-carbethoxy-1,2-dicyanoethyl)benzene was deposited as a yellow oil which solidified upon standing.

EXAMPLE 2—1,4-bis(2-carbethoxy-1,2-dicyanoethyl)benzene

The reaction conditions of Example 1 were repeated using 57.7 g (0.178 mole) of the previously prepared diester, 1,4-bis(2-carbethoxy-2-cyanoethenyl)benzene. The diester was added to 175 ml ethanol having 25 ml water added thereto, and kept in suspension by rapid stirring. To this stirred mixture 100 ml of an aqueous solution of sodium cyanide (26.2 g, 0.534 mole) was slowly added over 3 minutes. After 2 hours continuous stirring at ambient temperature the solid diester had completely dissolved.

Upon acidification with excess HCl the desired product 1,4-bis(2-carbethoxy-1,2-dicyanoethyl)benzene again precipitated and was separated from the aqueous layer by filtration.

EXAMPLE 3—1,3-bis(2-carbethoxyl-1,2-dicyanoethyl)benzene

A mixture of isophthaldehyde (2.68 g, 0.02 mole), ethyl cyanoacetate (4.6 g, 0.04 mole), piperidine (2 drops) and anhydrous methanol (50 ml) was stirred at room temperature for 5.5 hours. A white precipitate (5.5 g, 85 percent yield) was collected and identified as 1,3-bis(2-carbethoxy-2-cyanoethenyl)benzene.

The above prepared product (5.1 g, 0.015 mole) was suspended in 75 ml water. Sodium cyanide (2.36 g, 0.048 mole) was added with stirring at ambient temperature. After 2 hours the clear solution was acidified and the product extracted with methylene chloride. This fraction was washed with water, dried with anhydrous $MgSO_4$ and then evaporated to dryness yielding 5.1 g of a waxy white solid. Analysis by infrared absorption spectroscopy (IR) and nuclear magnetic resonance spectroscopy (NMR) confirmed the products identity as 1,3-bis(2-carbethoxy-1,2-dicyanoethyl)benzene.

EXAMPLE 4—1,4-bis(2-carbethoxy-1,2-dicyano-1-methylethyl)-benzene.

A mixture of p-diacetylbenzene (20.25 g, 0.125 mole), ethyl cyanoacetate (28.3 g, 0.25 mole), ammonium acetate (3.85 g) and acetic acid (10 g) was combined in a 500 ml glass round-bottom flask with toluene (150 ml) and refluxed for 12 hours. A Dean-Stark trap was employed to trap water formed during the reaction. Refluxing was discontinued and the solvent evaporated. The residue containing crude product was distilled under reduced pressure. One fraction, boiling point range 177° C.–195° C. (0.6 mm) amounting to 20.6 g was identified as predominately the 1:1 condensation product. A second fraction, boiling point ~200° C. yielded 18.2 g of 1,4-bis(2-carbethoxy-2-cyano-1-methylethenyl)benzene.

A portion of this second product weighing 9.29 g was heated at 85° C. for 2 hours in 50 ml water having dissolved therein sodium cyanide (5.12 g). After heating, the solution was stirred for 3 hours at room temperature. The diester slowly dissolved resulting in a clear light yellow solution. The solution was then acidified with excess concentrated HCl and the product extracted with chloroform. The product, 1,4-bis(2-carbethoxy-1,2-dicyano-1-methylethyl)benzene was identified by IR and NMR spectroscopy.

EXAMPLE 5—1,4-bis-2-(1,3-dicyanopropyl)benzene

Terephthaldehyde (53.6 g, 0.4 mole) and cyanoacetic acid (170 g, 2 moles) were combined in a round bottom flash with 350 ml of pyridine containing 20 ml piperidine. The mixture was then refluxed for about 15 hours. A yellow solution remained when refluxing ceased. After the solvent was removed by evaporation under reduced pressure a residue remained. This residue was washed with aqueous HCl followed by methanol and the product dried leaving 84.5 g (80.6% yield) of 1,4-bis-2-(1,3-dicyanopropyl) benzene.

Analysis of a sample of the product obtained from the above procedure by infrared (IR) and nuclear magnetic resonance (NMR) spectroscopy confirmed the identity of the above product.

EXAMPLE 6—1,3-bis[4-(2-carbethoxy-1,2-dicyanoethyl)phenoxy]-propane

The aldehyde, 1,3-bis(4-formylphenoxy)propane, was prepared by refluxing p-hydroxybenzaldehyde and 1,3-dibromopropane in an aqueous caustic solution. The recovered and recrystallized product (14.2 g, 0.05 mole) was combined with ethyl cyanoacetate (11.3 g, 0.1 mole) in methanol (100 ml) and about 1.0 ml of piperidine catalyst added. The mixture was stirred at room temperature for 24 hours resulting in the formation of white, solid precipitate.

Recovery by filtration and washing with methanol gave 21.1 g (89 percent yield) of the desired product, 1,3-bis[4-(2-carbethoxy-2-cyanoethenyl)phenoxy]propane. The structure was confirmed by NMR and IR analysis.

The desired tetracyanide derivative was formed by adding 100 ml of 2 molar aqueous NaCN to a mixture of the above compound (46.0 g, 0.097 mole), triethylamine (7 g) and ethanol (70 ml). The resulting mixture was stirred for 1 1/3 hours at 50° C. until the solid biscyanoethenyl ester had dissolved. Upon acidification the desired product separated and was recovered.

What is claimed is:

1. A bis-dicyanoalkyl arene compound of the formula

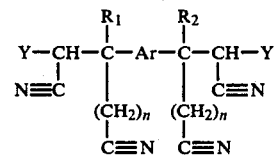

wherein Ar is a $C_{6-20}$ arylene radical selected from the group consisting of:

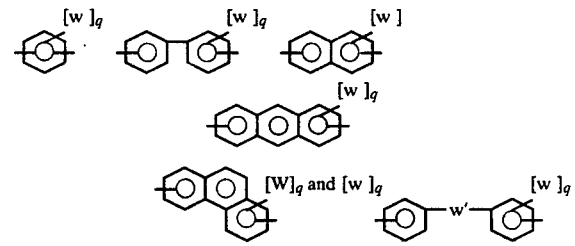

wherein w in each occurrence is halo, nitro, or a $C_{1-10}$ radical selected from alkyl, aryl, alkaryl, aralkyl, haloalkyl, haloaryl, aryloxy and alkoxy; q is an integer from zero to 4; and w' is oxygen, sulfur, alkylene, oxyalkylene, alkylenedioxy, or polyoxyalkylene; $R_1$, $R_2$ individually are hydrogen or alkyl, aryl, aralkyl, or alkaryl radicals containing up to 10 carbon atoms; Y is hydrogen or

where $R_3$ is an alkyl radical containing 1 to 10 carbon atoms; and both n's are zeros or ones, provided that when both n's are zeros, Y is

and when both n's are ones, Y is hydrogen.

2. A compound according to claim 1 wherein Ar is a phenylene radical.

3. A compound according to claim 2 that is 1,4-bis(2-carbethoxy-1,2-dicyano-1-methylethyl)benzene.

4. A compound according to claim 2 wherein $R_1$ and $R_2$ are hydrogen.

5. A compound according to claim 4 that is 1,3-bis(2-carbethoxy-1,2-dicyanoethyl)benzene.

6. A compound according to claim 4 that is 1,4-bis(2-carbethoxy-1,2-dicyanoethyl)benzene.

7. A compound according to claim 4 that is 1,4-bis-2-(1,3-dicyanopropyl)benzene.

8. A compound according to claim 4 that is 1,3-bis[4-(2-carbethoxy-1,2-dicyanoethyl)phenoxy]propane.

9. A process for making a substituted aromatic compound of the formula

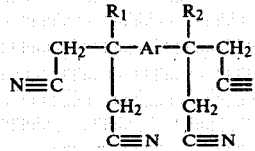

wherein Ar is a $C_{6-20}$ arylene radical selected from the group consisting of:

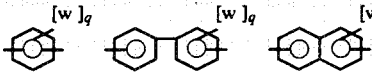

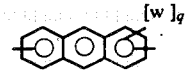

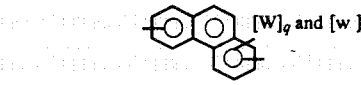

wherein w in each occurrence is halo, nitro, or a $C_{1-10}$ radical selected from alkyl, aryl, alkaryl, aralkyl, haloalkyl, haloaryl, aryloxy and alkoxy; q is an integer from zero to 4; and w' is oxygen, sulfur, alkylene, oxyalkylene, alkylenedioxy, or polyoxyalkylene; $R_1$, $R_2$ individually are hydrogen or alkyl, aryl, aralkyl, or alkaryl radicals containing up to 10 carbon atoms, comprising contacting cyanoacetic acid and an aromatic dicarboxyl compound in at least a 4:1 stoichiometric ratio at a temperature from about 80° C. to 200° C. in pyridine solvent in the presence of a catalytic amount of an amine catalyst and recovering the product.

10. The process according to claim 9 wherein the amine catalyst is piperidine.

* * * * *

UNITED STATES PATENT AND TRADEMARK OFFICE
CERTIFICATE OF CORRECTION

PATENT NO. : 4,239,694
DATED : December 16, 1980
INVENTOR(S) : Edmund P. Woo

It is certified that error appears in the above-identified patent and that said Letters Patent are hereby corrected as shown below:

Column 2, line 16; Column 6, line 27; and Column 8, line 1:

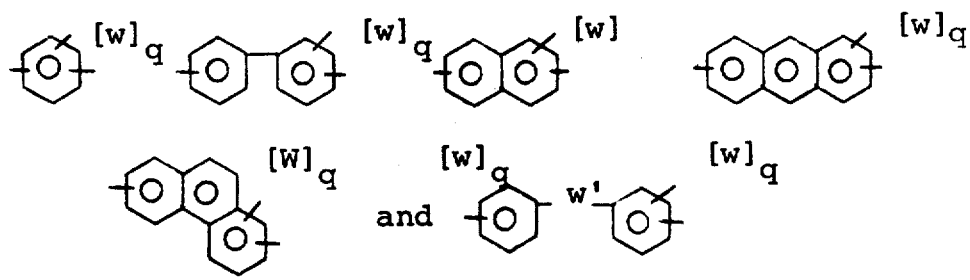

should read

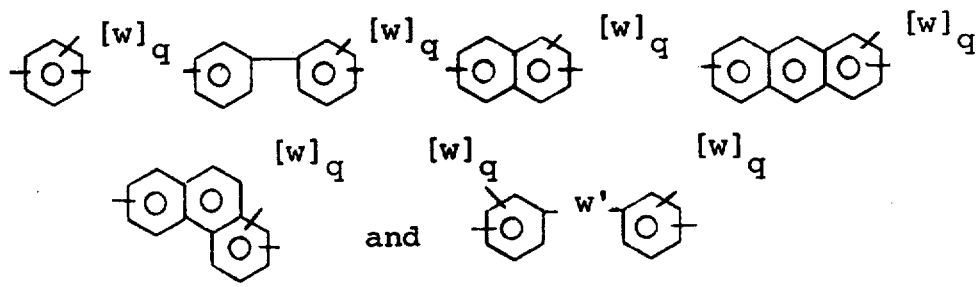

Column 2, line 40 "wherein" should read --where--.

UNITED STATES PATENT AND TRADEMARK OFFICE
CERTIFICATE OF CORRECTION

PATENT NO. : 4,239,694
DATED : December 16, 1980
INVENTOR(S) : Edmund P. Woo

It is certified that error appears in the above-identified patent and that said Letters Patent are hereby corrected as shown below:

Column 3, line 40 "oxy-2cyanoethenyl)arene," should read
--oxy-2-cyanoethenyl)arene,--

Column 4, line 62 "1,3-bis(2-carbethoxyl-" should read
--1,3-bis(2-carbethoxy--

Column 5, line 1 "above prepared" should read
--above-prepared--

Column 5, line 44 "flash" should read --flask--

Signed and Sealed this

Twenty-eighth Day of April 1981

[SEAL]

Attest:

RENE D. TEGTMEYER

Attesting Officer

Acting Commissioner of Patents and Trademarks